US006607498B2

United States Patent
Eshel

(10) Patent No.: US 6,607,498 B2
(45) Date of Patent: Aug. 19, 2003

(54) METHOD AND APPARATUS FOR NON-INVASIVE BODY CONTOURING BY LYSING ADIPOSE TISSUE

(75) Inventor: Yoram Eshel, Tel Aviv (IL)

(73) Assignee: Ultra Shape, Inc., Wilmington, DE (US)

(*) Notice: Subject to any disclaimer, the term of this patent is extended or adjusted under 35 U.S.C. 154(b) by 241 days.

(21) Appl. No.: 09/752,530

(22) Filed: Jan. 3, 2001

(65) Prior Publication Data
US 2002/0128592 A1 Sep. 12, 2002

(51) Int. Cl.⁷ .................................................. A61H 1/00
(52) U.S. Cl. .................................. 601/2; 601/1; 604/22
(58) Field of Search ........................... 601/2, 1; 604/22; 606/128, 169; 600/439; 310/334; 73/624

(56) References Cited

U.S. PATENT DOCUMENTS

| 4,605,009 A | * | 8/1986 | Pourcelot et al. ............ 600/109 |
| 4,938,216 A | | 7/1990 | Lele |
| 4,986,275 A | | 1/1991 | Ishida et al. |
| 5,005,579 A | | 4/1991 | Wurster et al. |
| 5,079,952 A | * | 1/1992 | Nakaso et al. ................. 73/624 |
| 5,080,102 A | | 1/1992 | Dory |
| 5,111,822 A | | 5/1992 | Dory |
| 5,143,063 A | | 9/1992 | Fellner |
| 5,143,073 A | | 9/1992 | Dory |
| 5,209,221 A | | 5/1993 | Reidlinger |
| 5,219,401 A | | 6/1993 | Cathignol et al. |
| 5,301,660 A | | 4/1994 | Rattner |
| 5,419,761 A | | 5/1995 | Narayanan et al. |
| 5,431,621 A | | 7/1995 | Dory |
| 5,507,790 A | | 4/1996 | Weiss |
| 5,526,815 A | | 6/1996 | Granz et al. |
| 5,618,275 A | | 4/1997 | Bock |
| 5,640,371 A | * | 6/1997 | Schmidt et al. ............. 367/153 |
| 5,827,204 A | | 10/1998 | Grandia et al. |
| 5,884,631 A | | 3/1999 | Silberg |
| 5,938,608 A | | 8/1999 | Bieger et al. |
| 6,039,048 A | | 3/2000 | Silberg |
| 6,071,239 A | | 6/2000 | Cribbs et al. |
| 6,086,535 A | | 7/2000 | Ishibashi et al. |
| 6,113,558 A | | 9/2000 | Rosenschein et al. |
| 6,206,873 B1 | | 3/2001 | Paolini et al. |
| 6,384,516 B1 | * | 5/2002 | Fraser ........................ 310/334 |

FOREIGN PATENT DOCUMENTS

GB  2 303 552  2/1997

OTHER PUBLICATIONS

Rod J. Rohrich, et al., "Comparative Lipoplasty Analysis of in Vivo–Treated Adipose Tissue", Plastic and Reconstruction Journal, 105:2152–2158, 2000.

* cited by examiner

Primary Examiner—Quang T. Van
(74) Attorney, Agent, or Firm—Hoffman, Wasson & Gitler, PC

(57) ABSTRACT

A method and apparatus for producing lysis of adipose tissue underlying the skin of a subject, by: applying an ultrasonic transducer to the subject's skin to transmit therethrough ultrasonic waves focussed on the adipose tissue; and electrically actuating the ultrasonic transducer to transmit ultrasonic waves to produce cavitational lysis of the adipose tissue without damaging non-adipose tissue.

23 Claims, 9 Drawing Sheets

METHOD AND APPARATUS FOR NON-INVASIVE BODY CONTOURING BY LYSING ADIPOSE TISSUE

FIELD AND BACKGROUND OF THE INVENTION

The present invention relates to a method and apparatus for the non-invasive ultrasound body contouring of a subject, particularly for the treatment of fat deformities by lysing adipose (fat) tissue.

Three methods are currently available for the treatment of fat deformities: Suction Assisted Lipoplasty [SAL]; Ultrasound Assisted Liposuction [UAL]; and External Ultrasound Assisted Liposuction [E-UAL].

These procedures are skill dependent such that the results depend primarily on the skill of the surgeon. The surgeon marks the areas to be treated on the skin in a manner resembling a topographic map; the higher innermost areas have more fat, and lower outer areas have less fat.

In SAL, a cannule is inserted through a small skin cut into the adipose tissue and the fat is suctioned by negative pressure applied through the cannule by a pump. The cannule is moved back and forth in different tissue levels covering the volume to be suctioned. The fat is torn and evacuated at the same time. Usually more then one skin cut is needed in each area to achieve satisfactory result, and to avoid tunneling under the skin.

This procedure is nonselective and tears also blood vessels, small nerves, and connective tissue. Hemmatomas and hypo-sensation in the treated areas are unavoidable side effects. Following the surgery, the patient is usually dressed with a pressure garment for 4–6 weeks. Pain is common and generally takes a few days to subside. The procedure can be carried out under local or general anesthesia in an operating room or office environment. However, most of the procedures are performed under general anesthesia because of the discomfort to the patient. The procedure lasts up to 3–4 hours, depending on the amount of fat to be suctioned and on the surgeon's skill. The volumes cleared in one session are usually 2–5 liters.

UAL was introduced by Zocchi, in 1991. Here, too, the same saline solution is first injected into the fat tissue. The cannule used in UAL has an ultrasonic probe at its tip. When energy is applied, the tissue next to the tip is destroyed by the "cavitational effect" as described more particularly below. The wet environment achieved by injecting the saline solution is mandatory for the cavitation effect to occur. The fat can be evacuated by the same cannule or by a different one after the ultrasonic lipolysis was accomplished. It is claimed to be selective to the fat. However, if the physician does not move the cannule constantly, the tissue next to the tip can be "burned", and skin, muscle or bone tissues can be damaged. Third degree skin burns are a notorious complication of the procedure. Moreover, the movement of the canule through the adipose tissue disrupts blood vessels, nerves, and connective tissues as in the SAL procedure. The ability to evacuate large volumes is the main reason for using the UAL technique. Physicians have reported volumes reaching 15–27 liters of fat suctioned in one session. The skin is claimed to retract better after UAL compared to SAL, leaving less folds post treatment.

E-UAL is a newer technique. It employs the usual SAL technique but adds a treatment with a therapeutic ultrasonic transducer usually used to relieve pain and joint problems. The therapeutic ultrasound is applied after a tumescent solution is injected. The claimed advantage of the procedure is the relative ease of SAL after ultra-sound is applied. However, the energy is non-focused at 1 MHz, and therefore heating is the mode of action. Since energy is applied to the skin and underlying tissues equally, overheating may occur. A known side effect is hyper-pigmentation of the skin due to a healing process that takes place at the heated area. Moreover, pain and discomfort are common. Rohrick et al, in Plastic and Reconstruction Journal 105:2152, 2000, showed that the cellular disruption after E-UAL is similar to the traditional SAL. Otherwise this procedure is equivalent to SAL.

A tissue can be non-invasively exposed to ultrasonic energy in a focused or a non-focused manner. When a non-focused transducer is used, all tissues between the transducer, and up to a certain fading distance where energy levels are lower than the therapeutic threshold, are exposed to the ultrasonic energy. When focused ultrasound is used, only the tissue at the focal range of the transducer is specifically affected while all other tissues, between the transducer and the focus or beyond, are spared.

There are two modes in which ultrasonic energy interacts with tissues; (1) by heating, and (2) by cavitation.

Heating is non-specific. There is no tissue differentiation in the heating process; all tissues within a certain spatial radius are affected.

Cavitation is a physical phenomenon in which low-pressure bubbles are formed and then collapse in a liquid. The cavitation phenomen depends on specific tissue characteristics when employed in a biological environment. This enables tissue differentiation for destruction. That is fat cells can be destroyed, while blood vessels, peripheral nerves, skin, muscle and connective tissue within the ultrasonic focus, as well as neighboring tissues such as listed above outside the focus, will remain intact.

U.S. Pat. No. 6,113,558, in which one of the joint inventors is the inventor in the present application, describes both an invasive method and apparatus, and a non-invasive method and apparatus, for using ultrasound devices for cavitationally lysing tissue for ablating material obstructing blood vessels. U.S. Pat. No. 5,827,204 discloses a multi-frequency ultrasound cavitation technique for dissolving thrombi, promoting blood clotting, and destroying malignant and benign tumors in living tissue. U.S. Pat. No. 5,143,063 discloses a technique for focussing radiant energy (the sole described example utilizing microwave) to remove adipose tissue. U.S. Pat. No. 5,219,401 discloses a technique for generating gas bubbles, e.g., by injecting a precursor of gas bubbles, and then provoking in implosion by high power acoustic waves to selectively destroy tissue. U.S. Pat. No. 5,419,761 discloses a liposuction technique including the insertion of a tube and the production of ultrasonic cavitation at the distal end of the inserted tube to remove adipose tissue. U.S. Pat. No. 5,618,275 discloses a method of penetrating a therapeutic agent through the skin by ultrasonic waves producing cavitation. U.S. Pat. No. 6,039,048 discloses a technique using thermal energy rather than cavitational energy, and which acts on connective tissues rather than fat tissues.

None of the foregoing techniques appears to be completely satisfactory for producing lysis of adipose tissue without damaging non-adipose tissue in a non-invasive manner.

OBJECTS OF THE INVENTION

An object of the present invention is to provide a non-invasive method and apparatus for using ultrasonic devices for the treatment of fat deformities by producing lysis of adipose tissue without damaging non-adipose tissue.

BRIEF SUMMARY OF THE INVENTION

According to one aspect of the present invention, there is provided a method for producing lysis of adipose tissue underlying the skin of a subject, comprising: applying at least one ultrasonic transducer to the subject's skin to transmit therethrough ultrasonic waves focussed on the adipose tissue; and electrically actuating the ultrasonic transducer or transducers to transmit waves of sufficient intensity to cause cavitation and lysis of said adipose tissue without damaging non-adipose tissue.

According to further features in the preferred embodiments of the invention described below, the electrical peak output power is preferably from 100 to 750 watts, more preferably from 150 to 350 watts; the periodic ultrasonic waves have a pulse length of 0.80–4.0 ms a frequency of 150–500 Khz, preferably 250 Khz, and a repetition period of 5–100 ms.

As will be described more particularly below, such an ultrasonic transducer may be slid over the skin to destroy the adipocytes membranes and nuclei of the adipose tissue, without damaging neighboring tissues, such as connective tissue, the skin, blood vessels, peripheral nerves, muscle fibers or bone. Also, the procedure can be carried out in any office setting without the need for an operating theatre and anesthesia.

According to another aspect of the present invention, there is provided apparatus for use in producing lysis of adipose tissue underlying the skin of a subject, comprising: a focussing-type ultrasonic transducer or transducers for application to the subject's skin; and an electrical signal generator having a controller therein for energizing the ultrasonic transducer to generate, and to transmit through the subject's skin, periodic ultrasonic waves producing cavitational lysis of the adipose tissue without damaging non-adipose tissue.

Further features and advantages of the invention will be apparent from the description below.

BRIEF DESCRIPTION OF THE DRAWINGS

The invention is herein described, by way of example only, with reference to the accompanying drawings, wherein.

DETERMINATION OF THE ULTRASONIC ENERGY PARAMETERS

Ultrasonic energy can be transmitted either in a continuous wave mode, or in pulses. In a continuous wave mode, there is no cessation in the flow of transmitted energy, and an increase in temperature is therefore inevitable. In the pulsed mode, the energy is delivered in bursts which can be controlled to produce a controlled lower temperature rise.

Figure 3A:
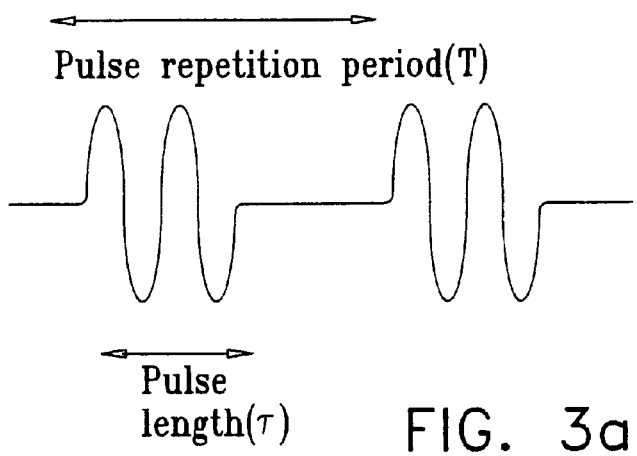
FIGS. 3a and 3b are diagrams illustrating, respectively, one form of periodic ultrasonic pulse outputted by the transducer, and certain characteristics of the transducer.

A pulsed wave can be characterized (besides the frequency and amplitude as in the continuous mode) by two parameters: the pulse length, and the pulse repetition period. The pulse length is defined here as the time in which the intensity is above the value needed for sustaining cavitation; between the pulses, the intensity is below that needed to sustain cavitation. The pulse repetition period is the time between two successive pulse initiations. FIG. 3a illustrates the type of pulse used in the experiments described below, this pulse being a constant amplitude pulse having 0 amplitude between pulses. The optimal ratio between the pulse length and pulse repetition period will cause a bubble to reach its maximal size and then collapse (cavitation). Further increase is redundant and contributes to heat generation rather than to the bubble collapse.

Thus, a change in pulse parameters can alter the mechanical effects exerted on different tissues. The selectivity of the ultrasound wave—the ability to destroy one tissue but at the same time keep other tissues intact-lies within the realm of pulse parameters selection. An increase in the pulse repetition period decreases the total energy delivered, and at certain values causes the cavitation to stop between two pulses even though it is an inertial phenomenon.

The amplitude needed for cavitation initiation is larger than that needed for cavitation sustaining as is the case in every inertial phenomenon. Therefore, the amplitude of the wave during the pulse does not have to be constant. As long as the amplitude is above the cavitation sustaining amplitude, it is still considered as part of the pulse.

There are a few considerations regarding the selection of frequency. First, lowering the frequency lowers the intensity (or actually the pressure—the square root of the intensity, which is the actual cause for the phenomena) needed for cavitation initiation. Consensus groups in the United States defined a parameter called Mechanical index (M.I.), which defines a value for mechanical (cavitational) damage.

$$M.I. = \frac{p}{\sqrt{f}}$$

Where f is the frequency and p is the pressure amplitude in the point.

There are no definite results on the value of mechanical index resulting in damage; therefore a mechanical index of 0.6 was defined as dangerous. Thus, if cavitation is to be used for destroying or damaging tissue, there is an interest for the lowest possible frequency. Second, there is an inverse relation between the frequency and the size of the focal area; therefore the frequency should be selected according to the specific focal area needed for the application.

In order to decide on the design parameters to be used, there are several considerations to be made.

Figure 3B:
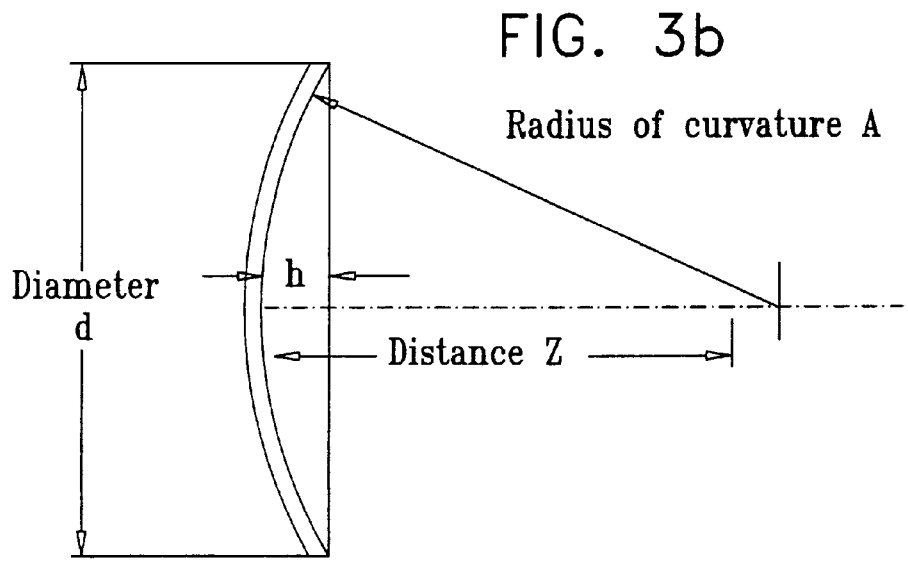

First, since focusing is needed, the most simple to construct solution is to use a hemispherical transducer. In such case, two input parameters are needed: the distance between the face of the transducer and the center of the focal area (Z in FIG. 3b), and the width of the focal area ($W_A$): Thus, to treat areas about 2 cm from the skin with a diameter ($W_A$) about 1 cm, Z=2 cm; and $W^A$=1 cm.

Kossof G. Analysis of Focusing Action of Spherically Curved Transducers Ultrasound In Med. & Biol. 5:359–365, 1979 derived the formula:

$$W_A = \frac{2.44\lambda A}{d}$$

Where A is the radius of curvature, d is the diameter of the transducer and $\lambda$ is the wavelength.

Following is one example of the foregoing parameters:

d=110 mm; λ=6 mm (f=250 Khz); A=62 mm resulting in $W^A$=8.25 mm

DESCRIPTION OF A PREFERRED EMBODIMENT

The Ultrasound System

Figure 1:
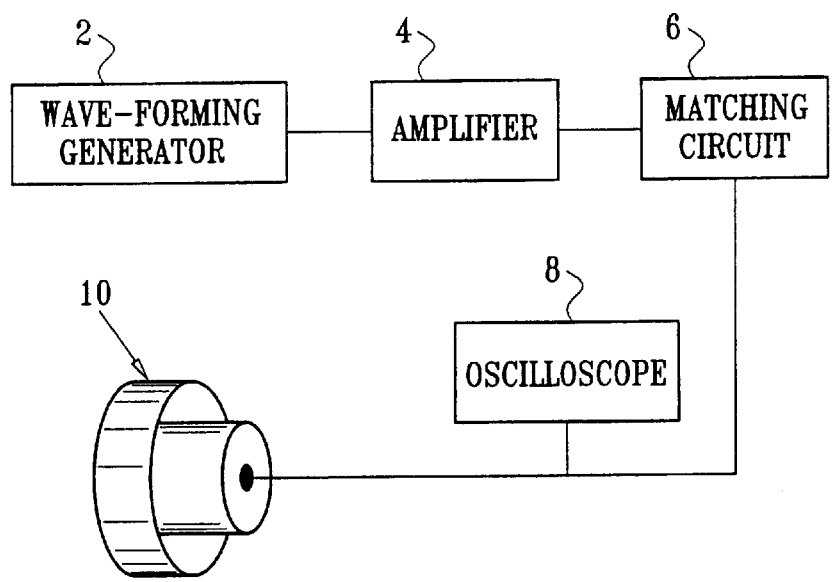
FIG. 1 is a block diagram illustrating one form of apparatus constructed in accordance with the present invention.
Figure 2A:
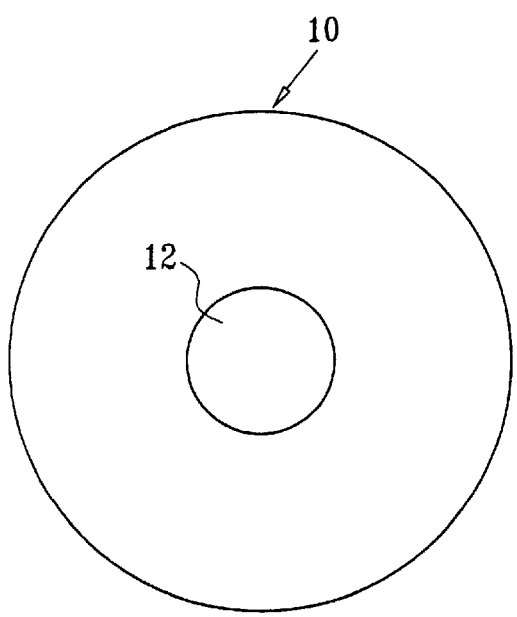
FIGS. 2a and 2b are side and front views, respectively, of the transducer in the apparatus of FIG. 1.
Figure 2B:
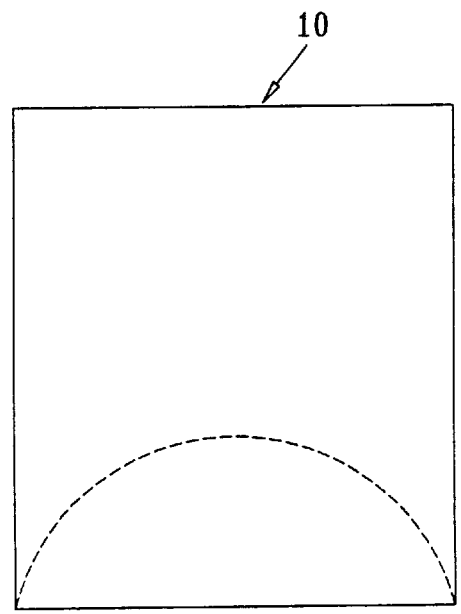

FIG. 1 is a block diagram illustrating one form of apparatus constructed in accordance with the present invention; and FIGS. 2a and 2b are front and side views, respectively, illustrating the focussed ultrasound transducer included in the apparatus of FIG. 1.

Thus, the apparatus illustrated in FIG. 1 includes a wave-forming generator 2, an amplifier 4, a matching circuit 6, an oscilloscope 8, and a focussing-type ultrasonic transducer 10, which is applied to the subject's skin to transmit therethrough ultrasonic waves focussed on the adipose tissue to be lysed.

The wave-forming generator 2 (e.g., TGA1320 TTI, USA) produces low power signals. The amplifier 4 (e.g., 700A, Amplifier Research, USA) increases the signal to a high power non-distorted signal. The matching circuit 6 (e.g., UltraShape Ltd, Israel) synchronizes the voltage and current phases on the transducer 10. The oscilloscope 8 (e.g., V1565, Hitachi, Japan) displays the voltage and current supplied to the transducer.

The ultrasound transducer 10 (e.g., 250 kHz, Imasonic, France), as illustrated in FIGS. 2a, 2b, has a hemispherical shape (radius of curvature 62 mm), and an external diameter of 136 mm. The transducer has a cylindrical hole 12 at its center for the placement of the imaging transducer (diameter of 34 mm). The sphere-like focus is 2 cm off the hemisphere plane and has a diameter of 1 cm. The concavity of the transducer was sealed with Poliuritan medium (Epusil U 105, Polymer Gvulot Ltd. Israel). The material had no effect on the intensity or characteristics of the signals produced by the transducer. The system was placed on the skin using ultrasound gel (Medi-Pharm, UK) for adequate acoustic coupling.

Fat Tissue Preparation

The fat and overlying skin were dissected down to the muscle fascia off a female pig, weighing approximately 100 kg. The dissection was carried out immediately after the animal sacrifice. The resulting sheath was approximately 2 cm in depth. The skin and fat were kept at 4° C. until used, no longer than 12 hr later. Ultrasound was applied, followed by instant excision of a cylinder (1 cm diameter, 2.0 cm high), containing skin, fat and muscle tissue (if existing in that volume). The specimen was fixed in 10% buffered formaldehyde (Bio-Lab, Israel) for 48 hr.

Histopathology

Standard histological techniques were used for the preparation of the specimens. Tissue embedding, sectioning and staining with Haematoxylin and Eosin, were done at Patho-Lab Ltd, Israel. Each section was cut longitudinally so the effect of ultrasonic energy along the therapeutic axis can be investigated.

Microscopic Analysis

Microscopic analysis was performed using light microscopy (Lieca), at ×50, ×100 and ×400 magnification. A video camera with PC-based image capturing software (CMS-1, A.M.S Ltd., Israel), connected to the microscope was used to record the pictures. Five fields in each slide were checked at each magnification. The magnitude of tissue damage was reflected by ghost cell appearance, membrane disruption and cyst formation, varying in size and extent. A magnification of ×400 was used to observe fine details of possible damage within the investigated field of view. Analysis was separately carried out by an attending pathologist and a scientist.

For the description, evaluation and analysis of the data, two scales were defined:

(1) Fat Lysis Score:

Damage to the fat cells was examined under ×50 magnification for maximal field size, and classified into 4 grades [FIGS. 11a–11d]:

Grade 0—no damage: intact, undamaged tissue with normal appearance (up to 10% damage might be technical and therefore will be counted as grade 0).

Grade 1—minimal damage: ghost cells, 2–3 cell-size microcysts, 10–25% damage.

Grade 2—large damage: ghost cells, large microcysts (5 cell-size) 26–50%.

Grade 3—massive damage: ghost cells, microcysts and larger cysts 51–100%, or total destruction of the fat tissue, shredded cells with broken membranes.

(2) Non-Fat Tissue Damage Score:

Grade 0—no damage: intact, undamaged tissue.

Grade 1—damage: a description of the damage will be added.

This particular score was selected since the desired ultrasonic therapeutic effect should absolutely harm no other tissue then the fat cells.

Possible damage to connective tissue, peripheral nerves and blood vessels (arteries and vein, as well as microvessels) within the fat tissue, or to neighboring tissues i.e., skin and muscle, was examined under ×50, ×100 and ×400. The larger magnifications were used to enable identification of even minor changes.

Results and Conclusions

Optimization of Pulse Parameters

For the establishment of a therapeutic index, the ratios among pulse characteristics had to be defined. Four characteristics were investigated: pulse length, pulse repetition period, total sonication time, and ultrasound peak electrical power. In order to establish the right ratios among the four parameters for superior fat tissue lysis, four separate trials were conducted. In each different trial, one parameter was changed and the others were kept constant.

In the first two trials pulse repetition rate and pulse length were studied. Electric peak power was kept constant at 150W (just above cavitation threshold), and total sonication time was kept constant at 5 sec.

In the first experiment the pulse length was kept constant at 1.6 milliseconds.

The pulse repetition period was increased from 5 to 100 milliseconds (5 miliseconds, 10 miliseconds and than in steps of 10 milliseconds. n=11).

In the second experiment the pulse repetition period was kept constant at 20 milliseconds. The pulse length was increased from 0.04 milliseconds to 4 milliseconds (0.04, 0.2, 0.4 and than in steps of 0.4 milliseconds. n=12).

The results of the fat lysis efficacy are summarized in Table 1:

TABLE 1

| exp | Pulse length [msec] | Pulse repetition period [msec] | Time of sonication [sec] | Electric peak output power [W] | Fat lysis score | Damage score |
|---|---|---|---|---|---|---|
| 1 | 1.6 | 5 | 5 | 150 | 0 | 0 |
|   | 1.6 | 10 | 5 | 150 | 3 | 0 |
|   | 1.6 | 20 | 5 | 150 | 3 | 0 |
|   | 1.6 | 30 | 5 | 150 | 3 | 0 |
|   | 1.6 | 40 | 5 | 150 | 3 | 0 |
|   | 1.6 | 50 | 5 | 150 | 3 | 0 |
|   | 1.6 | 60 | 5 | 150 | 3 | 0 |
|   | 1.6 | 70 | 5 | 150 | 2 | 0 |
|   | 1.6 | 80 | 5 | 150 | 1 | 0 |
|   | 1.6 | 90 | 5 | 150 | 0 | 0 |
|   | 1.6 | 100 | 5 | 150 | 0 | 0 |
| 2 | 0.04 | 20 | 5 | 150 | 0 | 0 |
|   | 0.2 | 20 | 5 | 150 | 0 | 0 |
|   | 0.4 | 20 | 5 | 150 | 0 | 0 |
|   | 0.8 | 20 | 5 | 150 | 1 | 0 |
|   | 1.2 | 20 | 5 | 150 | 2 | 0 |
|   | 1.6 | 20 | 5 | 150 | 3 | 0 |
|   | 2.0 | 20 | 5 | 150 | 3 | 0 |
|   | 2.4 | 20 | 5 | 150 | 3 | 0 |
|   | 2.8 | 20 | 5 | 150 | 3 | 0 |
|   | 3.2 | 20 | 5 | 150 | 3 | 0 |
|   | 3.6 | 20 | 5 | 150 | 3 | 0 |
|   | 4.0 | 20 | 5 | 150 | 3 | 0 |

Figure 11A:
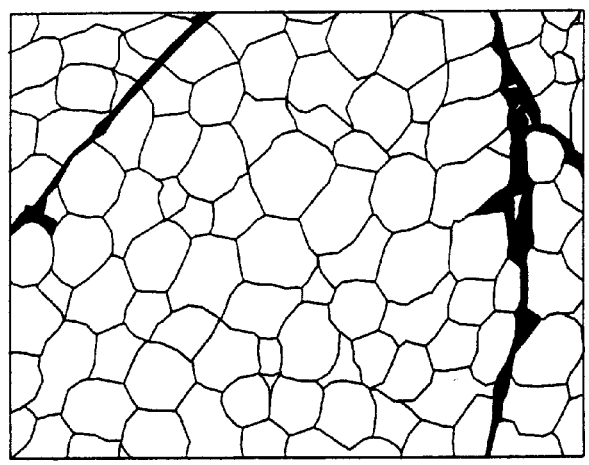
FIG. 11a is a control microphotograph.

Representative results showing control, and lysed fat area in all grades are shown in FIGS. 11a–11d, as follows:

FIG. 11a—Grade 0 Damage. A light microscopy representative photograph (×100) of untreated, control fat tissue. Tissue was fixed and stained with Haematoxylin & Eosin, as described under methods.

Figure 11B:
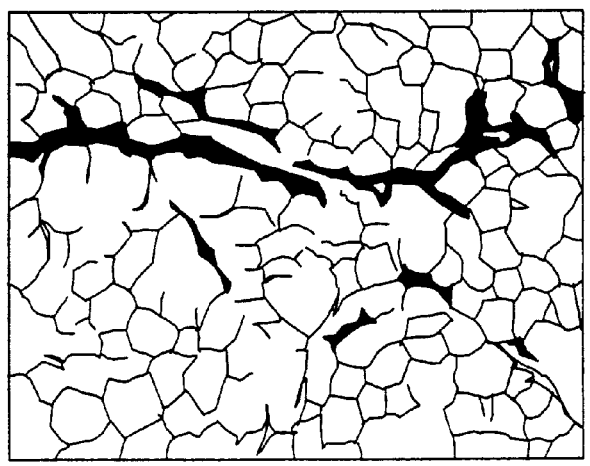
FIGS. 11b–11d are test-result microphotographs, illustrating the effects produced on adipose tissue when subjected to an irradiation treatment in accordance with the present invention as described herein.

FIG. 11b—Grade 1 Damage. Tissue was fixed and stained with Haematoxylin & Eosin, as described under methods. A light microscopy representative photograph (×100) of US-treated fat tissue (1.2 milisecond (msec) pulse length, 10 msec pulse repetition period, 200W and exposure time of 10 seconds.) Area measurements of the cysts formed show 15% damage.

Figure 11C:
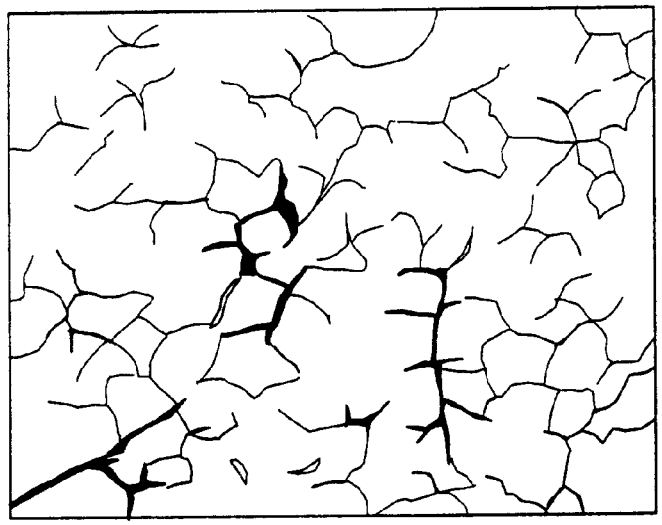

FIG. 11c—Grade 3 Damage. A light microscopy representative photograph (×100) of US-treated fat tissue (1.2 msec pulse length, 30 msec pulse repetition period, 300W and exposure time of 5 minutes). Tissue was fixed and stained with Haematoxylin & Eosin, as described under methods. Measurements of the damaged area show 40% damage.

Figure 11D:
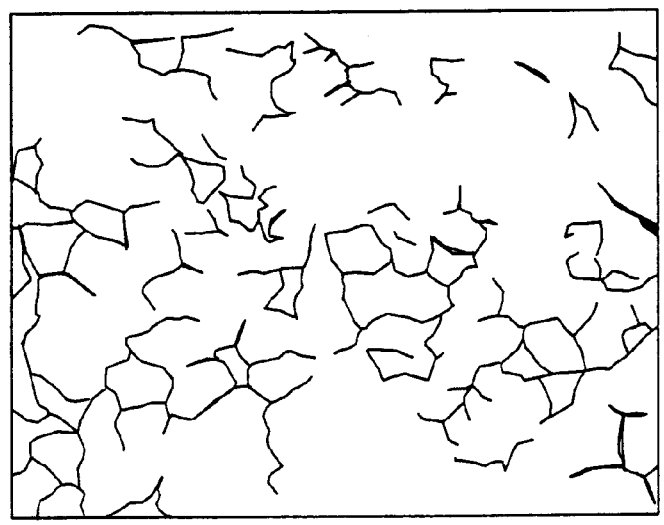

FIG. 11d—Grade 4 Damage. A light microscopy representative photograph (×100) of US-treated fat tissue (1.6 msec pulse length, 20 msec pulse repetition period, 300W and exposure time of 5 minutes). Tissue was fixed and stained with Haematoxylin & Eosin, as described under methods. Measurements of the damaged area show 80% damage.

Representing results showing intact neighboring tissues in a lysed-fat area are shown in FIGS. 12a–12d.

Figure 12A:
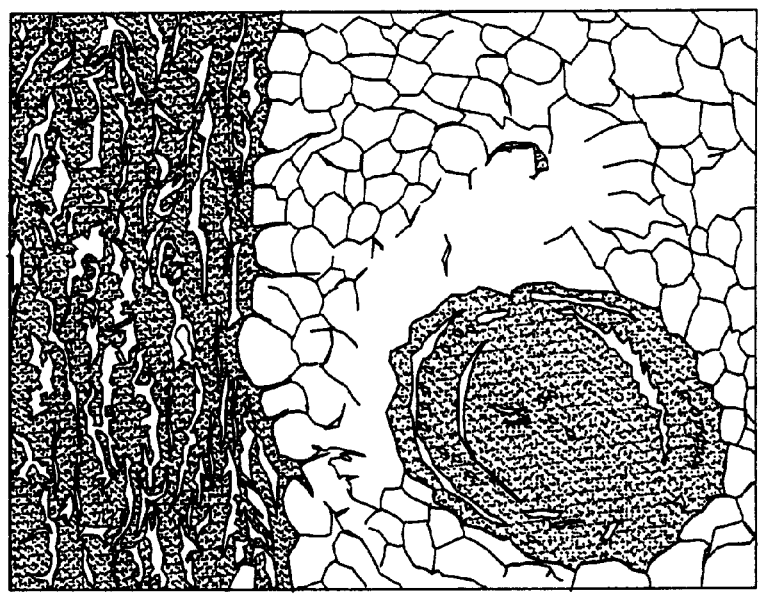
FIGS. 12a–12e illustrate various types of non-adipose tissues neighboring the treated adipose tissue which were left undamaged as a result of the described irradiation treatment.

FIG. 12a—Intact Skin Adnexa (Hair Follicle) In a Damaged Fat Tissue Field. Fat Tissue was US-irradiated with pulse length of 1.6 msec, 20 msec pulse repetition period, 250W and exposure time of 10 seconds. Following US treatment, tissue was fixed and stained with Haematoxylin & Eosin, as described under methods and photographed through a light microscope (×100).

Figure 12B:
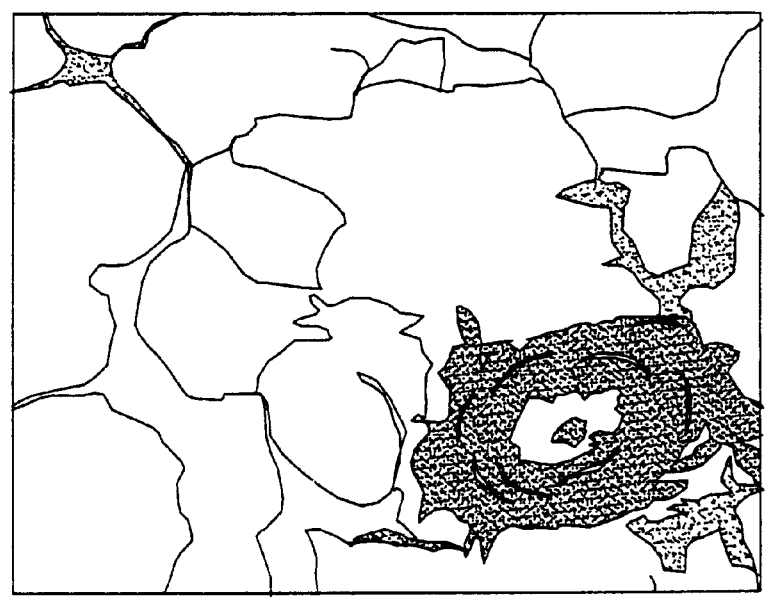

FIG. 12b—Intact Blood Vessel in Field of Massive Fat Damage. Fat tissue was US irradiated with pulse length of 1.6 msec, 20 msec pulse repetition period, 250W and exposure period of 10 seconds). Light microscopy photograph (×400) following fixation and staining with Haematoxylin & Eosin, as described under methods.

Figure 12C:

FIG. 12c—Intact Muscle in Field of Massive Fat Damage. Fat tissue was US irradiated with pulse length of 1.6 msec, 20 msec pulse repetition period, 300W and exposure period of 5 minutes). Light microscopy photograph (×100) following fixation and staining with Haematoxylin & Eosin, as described under methods.

Figure 12D:
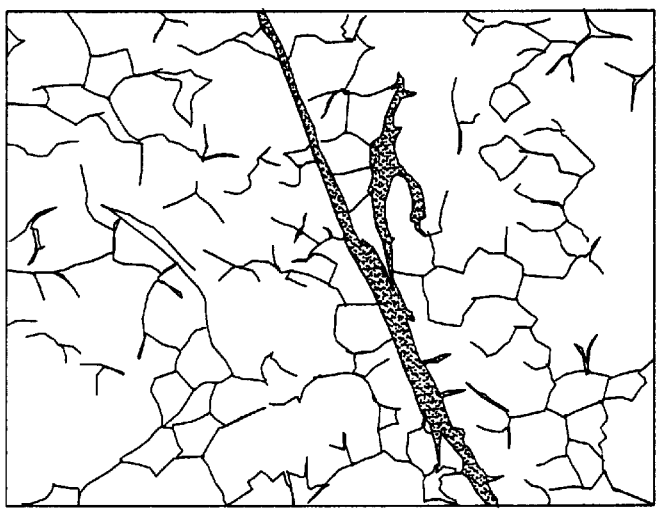

FIG. 12d—Intact Connective Tissue in a Highly Damaged Fat Field. Fat tissue was US irradiated with pulse length of 1.6 msec, 20 msec pulse repetition period, 300W and exposure period of 5 minutes). Light microscopy photograph (×100) following fixation and staining with Haematoxylin & Eosin, as described under methods.

Figure 12E:
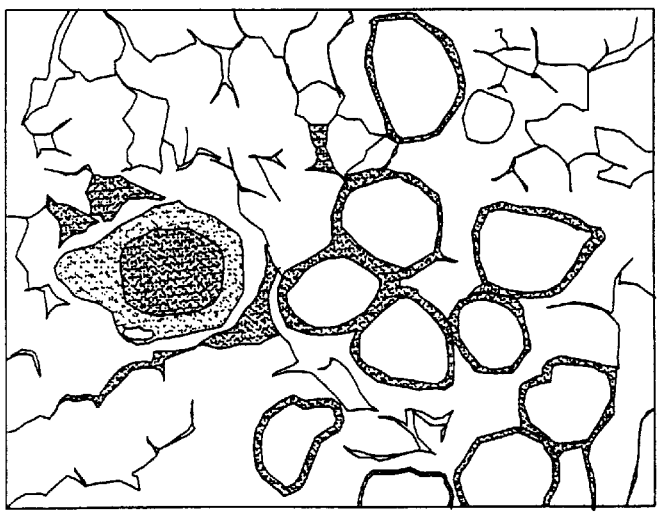

FIG. 12e—Intact Blood Vessel and Sweat Gland in a Damaged Fat Field.

Several conclusions can be made from the results of Table 1.

1. An increase of the pulse repetition period above 60 ms results in a decrease in the efficacy of the lysis.
2. There is a direct correlation between pulse length and efficacy of the lysis up to a saturated level at pulse length of 1.6 milliseconds.
3. No damage to any of the surrounding tissue can be observed.

Safety Margins

In the next trial, total sonication time and peak electrical power delivered were studied, while pulse length and pulse repetition rate were kept constant. Pulse length was kept constant at 1.6 milliseconds, and the pulse repetition period was kept constant at 20 milliseconds.

The power was increased 4 times from 150 W peak electric output to 300 W in steps of 50 W. Sonication time was increased 6 times at the following time periods: 0.1 sec, 0.5 sec, 1 sec, 2 sec, 5 sec, and 10 sec. (total of 24 experiments).

The results of the lysis efficacy are summarized in Table 2:

TABLE 2

| exp | Pulse length [msec] | Pulse repetition period [msec] | Time of sonication [sec] | Electric peak output power [W] | Fat lysis score | Damage score |
|---|---|---|---|---|---|---|
| 3 | 1.6 | 20 | 0.1 | 150 | 0 | 0 |
|   | 1.6 | 20 | 0.1 | 200 | 0 | 0 |
|   | 1.6 | 20 | 0.1 | 250 | 1 | 0 |
|   | 1.6 | 20 | 0.1 | 300 | 2 | 0 |
|   | 1.6 | 20 | 0.1 | 350 | 2 | 0 |
|   | 1.6 | 20 | 0.5 | 150 | 0 | 0 |
|   | 1.6 | 20 | 0.5 | 200 | 1 | 0 |
|   | 1.6 | 20 | 0.5 | 250 | 2 | 0 |
|   | 1.6 | 20 | 0.5 | 300 | 3 | 0 |
|   | 1.6 | 20 | 0.5 | 350 | 3 | 0 |
|   | 1.6 | 20 | 1 | 150 | 1 | 0 |
|   | 1.6 | 20 | 1 | 200 | 3 | 0 |
|   | 1.6 | 20 | 1 | 250 | 3 | 0 |
|   | 1.6 | 20 | 1 | 300 | 3 | 0 |
|   | 1.6 | 20 | 1 | 350 | 3 | 0 |
|   | 1.6 | 20 | 2 | 150 | 1 | 0 |
|   | 1.6 | 20 | 2 | 200 | 3 | 0 |
|   | 1.6 | 20 | 2 | 250 | 3 | 0 |
|   | 1.6 | 20 | 2 | 300 | 3 | 0 |
|   | 1.6 | 20 | 2 | 350 | 3 | 0 |
|   | 1.6 | 20 | 5 | 150 | 2 | 0 |
|   | 1.6 | 20 | 5 | 200 | 3 | 0 |
|   | 1.6 | 20 | 5 | 250 | 3 | 0 |
|   | 1.6 | 20 | 5 | 300 | 3 | 0 |
|   | 1.6 | 20 | 5 | 350 | 3 | 0 |

TABLE 2-continued

| exp | Pulse length [msec] | Pulse repetition period [msec] | Time of sonication [sec] | Electric peak output power [W] | Fat lysis score | Damage score |
|---|---|---|---|---|---|---|
| | 1.6 | 20 | 10 | 150 | 2 | 0 |
| | 1.6 | 20 | 10 | 200 | 3 | 0 |
| | 1.6 | 20 | 10 | 250 | 3 | 0 |
| | 1.6 | 20 | 10 | 300 | 3 | 0 |
| | 1.6 | 20 | 10 | 350 | 3 | 0 |

Several conclusions can be deduced from the results summarized in Table 2:
1. US irradiation resulted in specific fat tissue damage, leaving intact surrounding tissues, as well as tissues or organs in the irradiated region.
2. When low-power US is applied (150W), a limited fat lysis occurs.
3. In 150W, 10-fold increase in exposure time (1 to 10 sec) resulted in only a 2-fold increase in the level of damage, which did not exceed 50%.
4. Irradiation in US power of 200W and higher, results in maximal fat lysis, even at very short exposures (from 1 sec and more).
5. From 250W and up, even as short exposure as 0.1 sec resulted in some fat lysis.
6. In 350W, even exposure time of 0.5 sec resulted in maximal specific fat lysis, leaving surrounding tissues intact.

Discussion

An ideal body-contouring treatment should have the following characteritics:
1. non invasive;
2. harmless;
3. very wide therapeutic index;
4. very low complication rate;
5. enable treatment planning;
6. very predictable results;
7. match the treatment plan;
8. easy and short recovery and healing time;
9. painless;
10. short treatment time;
11. capability of full monitoring with safety mechanisms activated automatically;
12. minimize dependency on operator skill;
13. repeatability of treatments periodically when needed.

Examination of the above-described non-invasive ultrasonic body contouring method indicates that many of these characteristics are attainable. Thus, the method is non-invasive; the preliminary results show destruction of fat tissue, while skin, muscle, connective tissue, nerves and blood vessels were spared (Tables 1 and 2; FIGS. 11a–11d; FIGS. 12a–12e). It has been demonstrated that the device has a measurable therapeutic index. The treatment time is short, i.e. each pulse treating a volume of 1 cm$^3$ of fat lasts 10 seconds or less. The system does not require the skill of a trained plastic surgeon and suffices with basic technical skills.

It has been shown in the above cavitation threshold, that a significant lysis of adipose cells is achieved. The lysed adipose cells may be removed by body absorption, which may be accelerated by body massage or administration of drugs, as known. The lysed adipose cells may also be removed by liposuction.

Variations

While the apparatus described above utilized a curved-design type of focussing transducer, it will be appreciated that other focussing-type transducers may be used. FIGS. 4–9 illustrate other constructions of focussing-type transducers that may be used.

Figure 4:
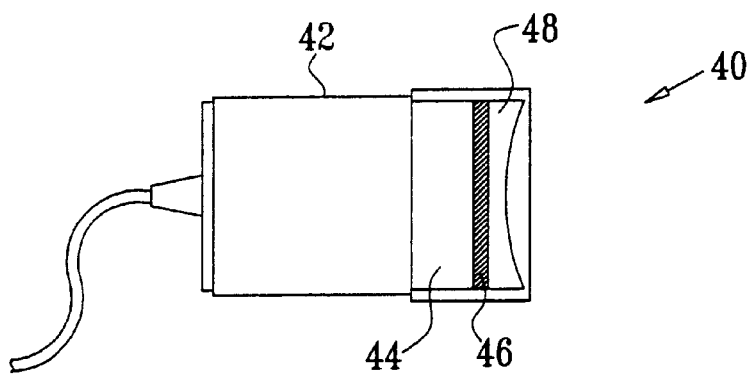
FIGS. 4–9 illustrate other types of focusing transducers that may be used.

Thus, FIG. 4 illustrates an acoustic-lens type of focussing transducer 40 including a housing 42, backing material 44, a planar piezoelectric element 46, and a focussing lens 48.

Figure 5:
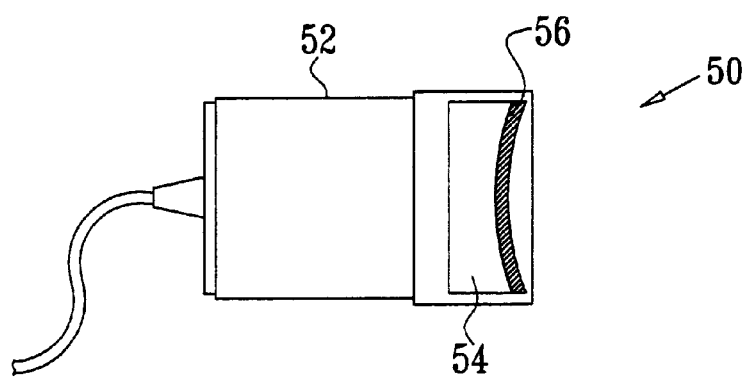

FIG. 5 illustrates a focussing transducer 50 including a housing 52, backing material 54, and a curved piezo-electric element 56.

Figure 6:
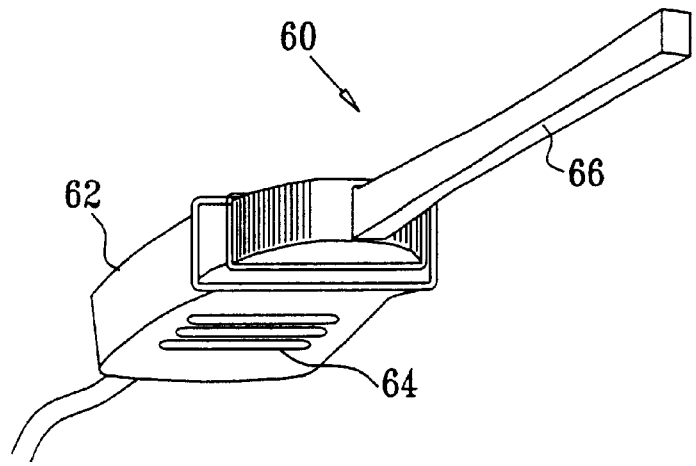

FIG. 6 illustrates a focussing transducer, generally designated 60, including a housing 62 and a linear array of focussing elements 64 in which the focussing is created by changing the phase of the elements in order to generate an ultrasonic wave emerging along one beam line 66.

Figure 7:
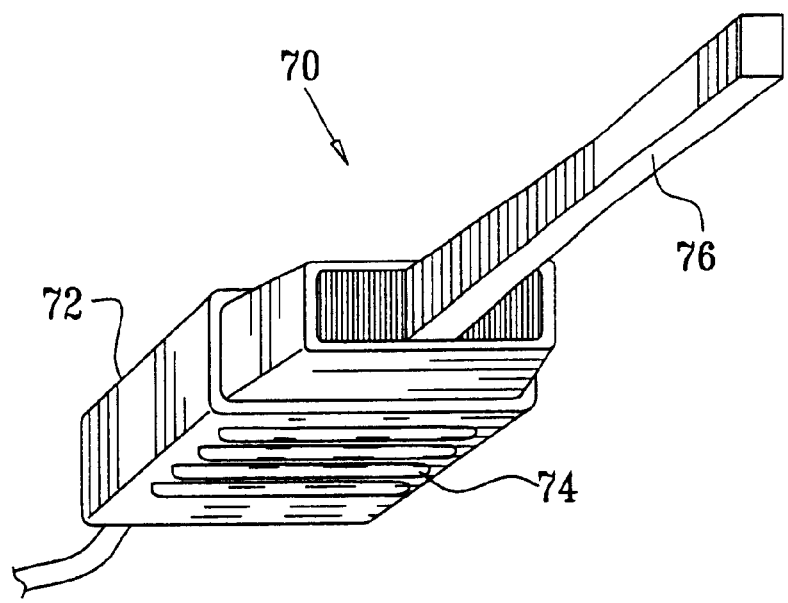

FIG. 7 illustrates a focussing transducer 70 including a housing 72 and a rectilinear array of piezoelectric elements 74 in which the focussing is created by changing the phase of the elements in order to focus them along a beam line 76.

Figure 8:
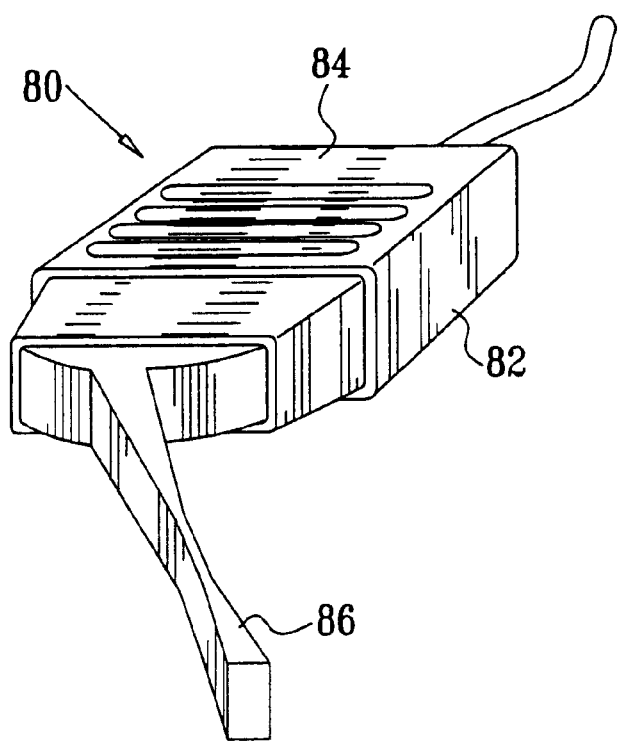

FIG. 8 illustrates a focussing type transducer 80 including a housing 82 and a linear array of piezoelectric elements 84 whose phases are controlled in order to produce an ultrasound pulse travelling off at an angle 86.

Figure 9:
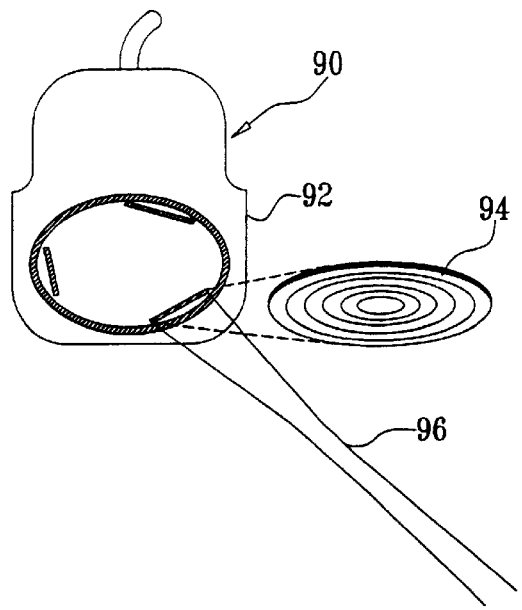
Figure 10:
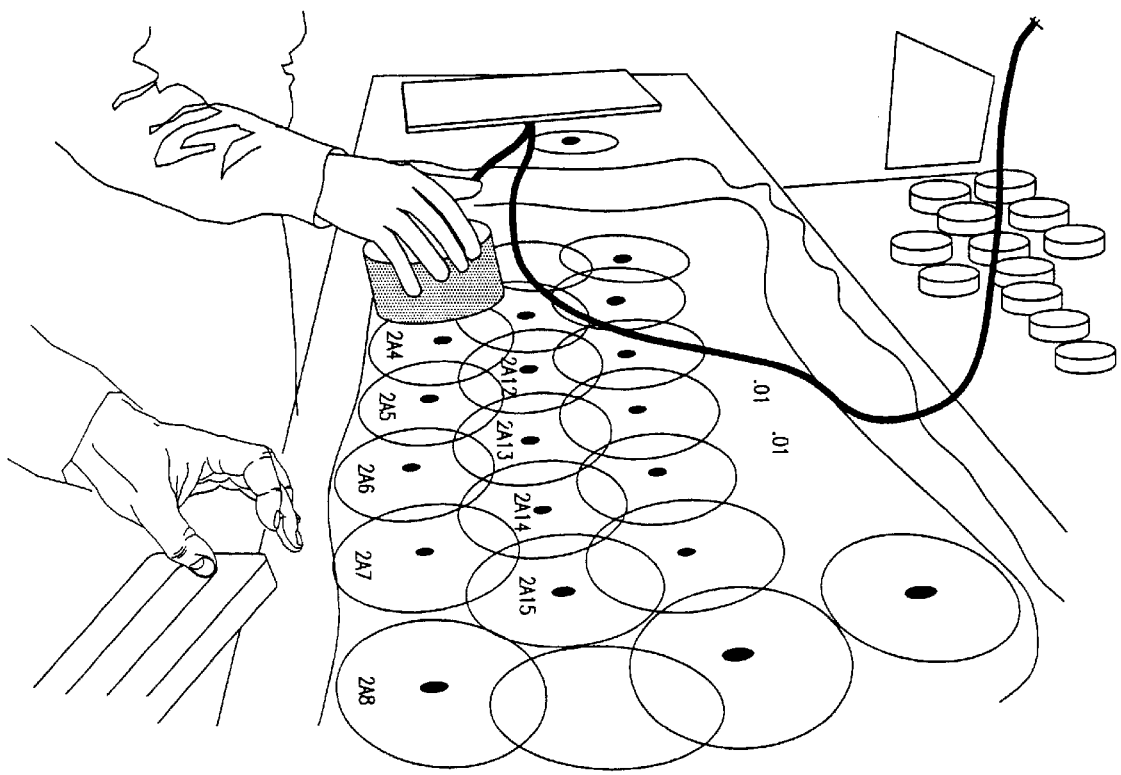
FIG. 10 illustrates the manner in which a swine's skin was marked to define the areas irradiated by the ultrasound transducer in accordance with the procedures described below.

FIG. 9 illustrates a focussing transducer 90 including a housing 92 and annular arrays of piezoelectric elements 94 producing an ultrasound pulse travelling along a beam line 96 perpendicular to the surface of the array.

Any of the above-mentioned embodiments of the invention can be implemented in a way that more than one transducer is used either in the same focus area or in different focus areas.

It will be appreciated that variations may also be made in the pulse shape; that the amplitude of the waves in the pulse does not have to be constant; and that the amplitude during times where there is no cavitation does not have to be 0, but need be only below the cavitation sustaining value.

It will also be appreciated that the transducer used to produce the cavitations may also be used to produce an image of the adipose tissue and adjacent non-adipose tissue for viewing during the administration of the treatment.

While the invention has been described with respect to several preferred embodiments, it will be appreciated that these are set forth merely for purposes of example, and that many other variations, modifications and applications of the invention may be made.

What is claimed is:

1. A method for producing lysis of adipose tissue underlying the skin of a subject, comprising:
   applying at least one ultrasonic transducer to the subject's skin to transmit therethrough ultrasonic waves focused on said adipose tissue; and
   electrically actuating said ultrasonic transducer to transmit periodic ultrasonic waves of sufficient intensity to cause cavitation and lysis of said adipose tissue without damaging adjacent non-adipose tissue.

2. The method according to claim 1, wherein the electrical peak output power of said ultrasonic waves is from 100–750 watts.

3. The method according to claim 2, wherein said peak output power is 150–350 watts.

4. The method according to claim 1, wherein said periodic ultrasonic waves have a pulse length of 0.80–4.0 ms.

5. The method according to claim 4, wherein said pulse length is 1.0–2.0 ms.

6. The method according to claim 1, wherein said periodic ultrasonic waves have a pulse repetition period of 5–100 ms.

7. The method according to claim 6, wherein said periodic ultrasonic waves have a pulse repetition period of 10–60 ms.

8. The method according to claim 7, wherein said periodic ultrasonic waves have a pulse repetition period of 20 ms.

9. The method according to claim 1, wherein said ultrasonic transducer is applied to the external surface of the subject's skin at a plurality of locations each for a period of 0.1–30 secs.

10. The method according to claim 1, wherein the electrical peak output power of said ultrasonic waves is from 100–750 watts, the periodic ultrasonic waves have a pulse length of 0.80–4.0 ms, and said ultrasonic transducer is applied to the external surface of the subject's skin for a period of 0.1–10 secs at a location overlying said adipose tissue.

11. The method according to claim 10, wherein said periodic ultrasonic waves have a pulse length of 1.6 ms.

12. The method according to claim 11, wherein a pulse repetition period of said periodic ultrasonic waves is 10–60 ms.

13. The method according to claim 1, wherein the lysed adipose tissue is removed by body absorption accelerated by body massage.

14. The method according to claim 1, wherein the lysed adipose tissue is removed by liposuction.

15. The method according to claim 1, wherein said transducer is also used to produce an image of the adipose tissue and adjacent non-adipose tissue.

16. Apparatus for use in producing lysis of adipose tissue underlying the skin of a subject, comprising:

a focusing-type ultrasonic transducer for application to the subject's skin; and an electrical signal generator having a controller therein for energizing the ultrasonic transducer to generate, and to transmit through the subject's skin, periodic ultrasonic waves producing cavitational lysis of the adipose tissue without damaging non-adipose tissue.

17. The apparatus according to claim 16, wherein the focusing-type electronic transducer is of a hemispherical shape.

18. The apparatus according to claim 16, wherein the focusing-type electronic transducer includes a planar piezoelectric element and a focusing lens.

19. The apparatus according to claim 16, wherein the focusing-type electronic transducer includes a curved piezoelectric element.

20. The apparatus according to claim 16, wherein the focusing-type electronic transducer includes an array of focusing elements in which the focusing is created by changing the phase of the elements in order to generate an ultrasonic wave emerging along one beam line.

21. The apparatus according to claim 16, wherein the focusing-type electronic transducer includes a rectilinear array of piezoelectric elements in which the focusing is created by changing the phase of the elements in order to focus them along a beam line.

22. The apparatus according to claim 16, wherein the focusing-type electronic transducer includes a linear array of piezoelectric elements whose phases are controlled in order to produce an ultrasound pulse traveling at an angle.

23. The apparatus according to claim 16, wherein the focusing-type electronic transducer includes an annular array of piezoelectric elements producing an ultrasound pulse traveling along a beam line perpendicular to the surface of the array.

* * * * *